(12) United States Patent
Tiao et al.

(10) Patent No.: US 8,514,390 B2
(45) Date of Patent: Aug. 20, 2013

(54) OPTICAL EQUIPMENT AND REGISTRATION METHOD

(71) Applicant: Industrial Technology Research Institute, Hsinchu (TW)

(72) Inventors: Kuo-Tung Tiao, Zhubei (TW); Jau-Jiu Ju, Zhudong Township, Hsinchu County (TW); Guo-Zua Wu, Taichung (TW); Tai-Ting Huang, Hsinchu (TW); Yuan-Chin Lee, Hsinchu (TW); Rung-Ywan Tsai, Guishan Township, Taoyuan County (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 13/646,026

(22) Filed: Oct. 5, 2012

(65) Prior Publication Data

US 2013/0094018 A1 Apr. 18, 2013

Related U.S. Application Data

(60) Provisional application No. 61/544,318, filed on Oct. 7, 2011.

(30) Foreign Application Priority Data

Jun. 13, 2012 (TW) .............................. 101121171 A

(51) Int. Cl.
   *G01N 21/00* (2006.01)
   *G01N 21/47* (2006.01)
(52) U.S. Cl.
   USPC .................. 356/237.5; 356/237.1; 356/237.2; 356/237.4; 356/237.3

(58) Field of Classification Search
   USPC ........ 356/237.1–237.5, 392–394; 250/458.1, 250/459.1; 382/144, 145, 149, 154
   See application file for complete search history.

(56) References Cited

U.S. PATENT DOCUMENTS

| 4,740,708 | A | * | 4/1988 | Batchelder | ............... | 250/559.41 |
| 4,748,335 | A | * | 5/1988 | Lindow et al. | ........... | 250/559.22 |

(Continued)

FOREIGN PATENT DOCUMENTS

| CN | 1285512 | 2/2001 |
| CN | 1875261 | 12/2006 |

(Continued)

OTHER PUBLICATIONS

English language translation of abstract of JP06-058719 (published Mar. 4, 1994).

(Continued)

*Primary Examiner* — Sang Nguyen
(74) *Attorney, Agent, or Firm* — McClure, Qualey & Rodack, LLP

(57) ABSTRACT

An optical equipment for inspecting and addressing a specimen is disclosed. The optical equipment comprises an optical device and a processing module. The optical device comprises a light source, a sample inspecting device and an address detecting device. The sample inspecting device comprises a first objective lens and a first detector. A beam is focused on a sample placed in an inspected site of a specimen by the first objective lens. The address detecting device comprises a second objective lens and a second detector. A beam is focused on the address coding site by the second objective lens. The processing module controls the beam to be focused on the sampling points of the inspected site to generate first optical signals, and simultaneously controls the beam of the light source to be focused on the corresponding address codes of the address coding site to generate second optical signals.

20 Claims, 11 Drawing Sheets

(56) References Cited

U.S. PATENT DOCUMENTS

| | | | |
|---|---|---|---|
| 5,777,729 A * | 7/1998 | Aiyer et al. | 356/237.1 |
| 5,844,709 A | 12/1998 | Rabinovich et al. | |
| 5,922,617 A * | 7/1999 | Wang et al. | 436/518 |
| 6,320,660 B1 | 11/2001 | Ju et al. | |
| 7,154,598 B2 | 12/2006 | Montagu et al. | |
| 7,433,031 B2 * | 10/2008 | Xu et al. | 356/237.2 |
| 7,507,957 B2 * | 3/2009 | Fujihira et al. | 250/306 |
| 7,772,569 B2 * | 8/2010 | Bewersdorf et al. | 250/458.1 |
| 2005/0007577 A1 * | 1/2005 | Engelhard et al. | 356/124 |
| 2005/0068057 A1 * | 3/2005 | Iwasaki et al. | 324/770 |
| 2005/0231717 A1 * | 10/2005 | Hsu et al. | 356/328 |
| 2007/0230770 A1 * | 10/2007 | Kulkarni et al. | 382/149 |
| 2008/0024794 A1 * | 1/2008 | Miyazaki et al. | 356/612 |
| 2008/0174765 A1 | 7/2008 | Tanikawa et al. | |
| 2009/0141278 A1 | 6/2009 | Tenney | |

FOREIGN PATENT DOCUMENTS

| | | |
|---|---|---|
| JP | 06-058719 | 3/1994 |
| JP | 07-159119 | 6/1995 |
| TW | 160926 | 6/1991 |
| TW | 436608 | 5/2001 |
| TW | 546549 | 8/2003 |
| TW | I247894 | 1/2006 |

OTHER PUBLICATIONS

English language translation of abstract of JP 07-159119 (published Jun. 23, 1995).

English language translation of abstract of CN 1285512 (published Feb. 28, 2001).

English language translation of abstract of TW 436608 (published May 28, 2001).

English language translation of abstract of TW 546549 (published Aug. 11, 2003).

English language translation of abstract of TW I247894 (published Jan. 21, 2006).

English language of translation of abstract of CN 1875261 (published Dec. 6, 2006).

Potyrailo, R.A., et al.; "Quantitative Chemical Analysis using DVDs and Conventional Computer Optical Disk Drives;" IEEE; 2007; pp. 1115-1118.

Lyu, H.C., et al.; "A Novel Digital Scanning Microscope;" SPIE-OSA; vol. 8086; 2011; pp. 1-6.

Kim, K.H., et al.; "DNA Microarray Scanner with a DVD Pick-Up Head;" Current Applied Physics 8; 2008; pp. 687-691.

Kasukurti, A., et al.; "Single-Cell Isolation using a DVD Optical Pickup;" 2011; pp. 10377-13086.

Ferrari, J.A., et al.; "Application of DVD/CD Pickup Optics to Microscopy and Fringe Projection;" American Journal of Physics 78; 2010; pp. 602-607.

Shimomura, T., et al.; "Developement of a Compact Optical System for Microarray Scanning using a DVD Pickup Head;" Review of Scientific Instruments 79; 2008; pp. 1-7.

* cited by examiner

OPTICAL EQUIPMENT AND REGISTRATION METHOD

This application claims the benefits of provisional application Ser. No. 61/544,318, filed Oct. 7, 2011, as well as Taiwan application Serial 101121171, filed Jun. 13, 2012, the disclosure of which are incorporated by reference herein in its entirety.

TECHNICAL FIELD

The disclosure relates in general to an optical equipment, and more particularly to an optical equipment with specimen registration function.

BACKGROUND

When one sample is inspected by optical method, the sampling points of the sample are normally consisted of many different and non-fixed points rather than one single point. Due to the absence of any regular feature points available on the sample for reference, the actual addresses of the sampling points may not be obtained by only using an open-loop motion method for sampling. Furthermore, if image capturing or signal detecting by using an optical scanning device equipped with a position feedback sensor, such as a laser galvo mirror equipped with a galvanometer or an optical encoder or a magnetic encoder, the position information of the optical scanning device is feedback. Then, the actual addresses of the sampling points on the sample are calculated by the feedback position information of the optical scanning device and the non-linear and complicated coordinate transformation formulas.

The said addresses of the sampling points are different and separated from the said feedback position information of the optical scanning device by a distance being far larger than the scale of the sampling displacement. Consequently, the position errors are amplified in the coordinate transformation, and result in differences between the calculated values and the actual addresses of the sampling points. Besides, for a live sample which needs to be periodically observed over a period of time, once the specimen is removed from the equipment and then replaced to the equipment again, position change and image offset will occur.

SUMMARY

The disclosure is directed to an equipment with a sample inspecting device and an address detecting device. The equipment simultaneously obtains sample inspected information and its corresponding address information, so as to register each inspected result and its address of all the sampling points on the sample.

According to one embodiment, an optical equipment for inspecting and addressing a sample is disclosed. The optical equipment comprises an optical device and a processing module, the optical device comprises a light source, a sample inspecting device and an address detecting device. The sample inspecting device comprises a first objective lens and a first detector. A beam of the light source is focused on a sample placed on the inspected site of a specimen by the first objective lens. The address detecting device comprises a second objective lens and a second detector. A beam of the light source is focused on the address coding site by the second objective lens. The processing module controls the beam of the light source to be focused on different sampling points of the inspected site to generate a several first optical signals, simultaneously controls the beam of the light source to be focused on those corresponding address codes of the address coding site to generate several second optical signals. All of the relative positions between each sampling point and its corresponding address code are the same, so as to obtain the registered image or signal information of the specimen according to the first and the second optical signals.

According to another embodiment, an address registration method is disclosed. The method comprises the following steps. An optical equipment comprising an optical device and a processing module, is provided. The optical device comprises a light source, a sample inspecting device and an address detecting device. The sample inspecting device comprises a first objective lens and a first detector. The address detecting device comprises a second objective lens and a second detector. A specimen comprising an inspected site and an address coding site, is provided, wherein the inspected site has several sampling points and the address coding site has several address codes, and a sample is placed on the inspected site. A beam of the light source is focused on the sample by the first objective lens, and a beam of the light source is focused on the address coding site by the second objective lens simultaneously. The processing module controls the beam of the light source to be focused on different sampling points of the sample so as to generate several first optical signals, and controls the beam of the light source to be focused on those corresponding address codes of the address coding site so as to generate several second optical signal. All of the relative positions between each sampling point and its corresponding address code are the same, so as to obtain the registered image or signal information of the specimen according to the first and the second optical signals.

Figure 1:
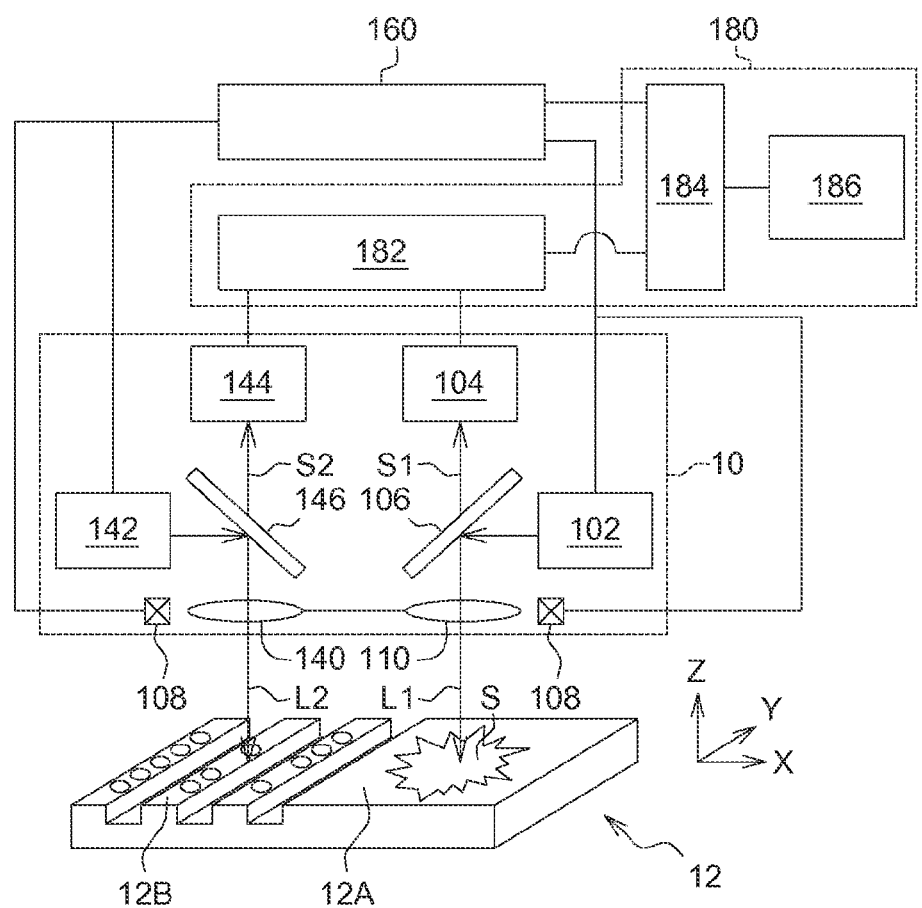
FIGS. 1~3 show schematic diagrams of an optical equipment according to different embodiments of the disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

DETAILED DESCRIPTION

Figure 2:
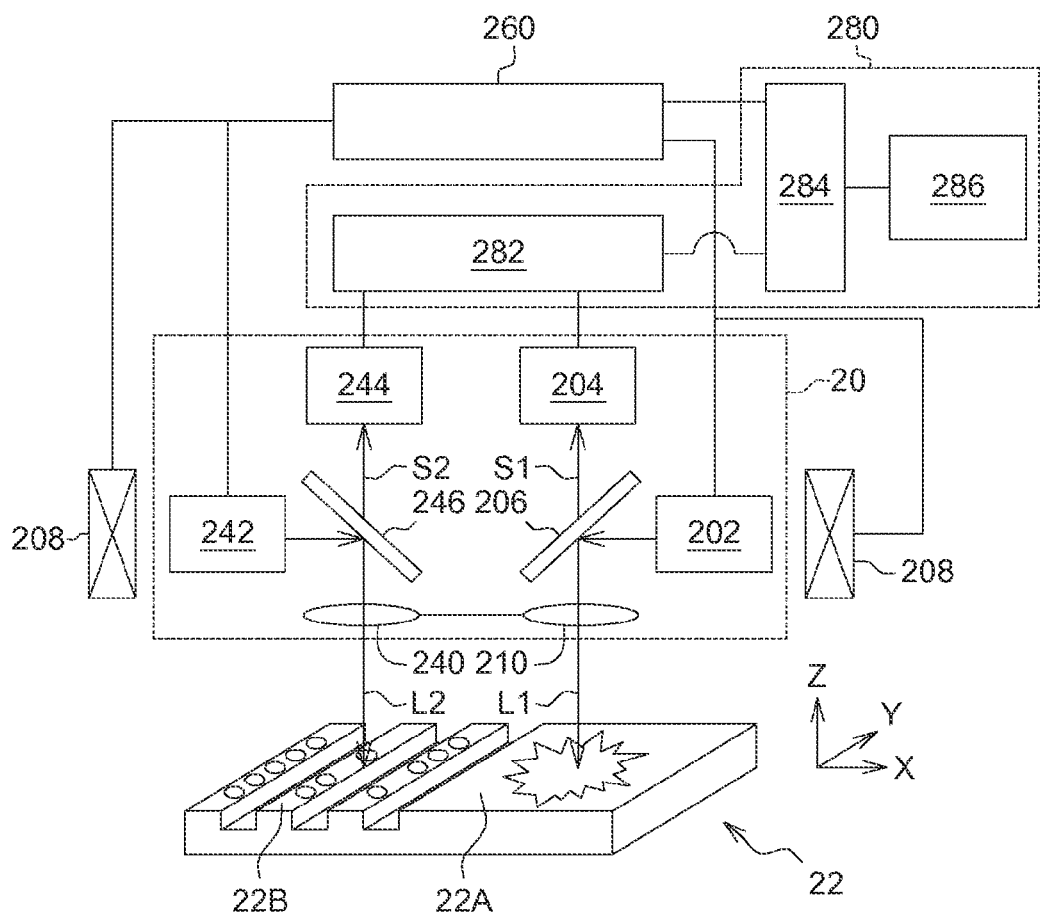
Figure 3:
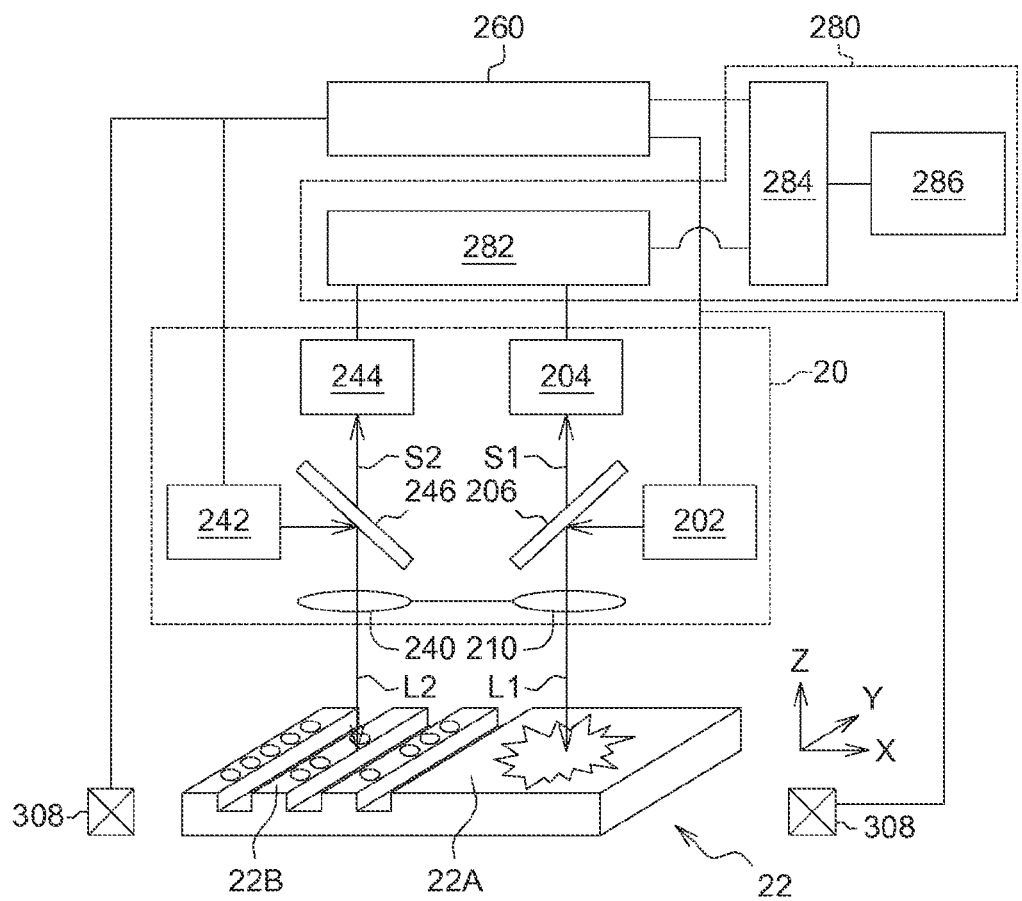

FIGS. 1~3 respectively show a schematic diagram of an optical equipment according to different embodiments of the disclosure. Referring to FIG. 1. The optical equipment 1 comprises an optical device 10, a controller 160 and a processing module 180. The controller 160 is such as a circuit comprising an actuator 108, and the controller 160 can be integrated within the processing module 180. The optical device 10 comprises a sample inspecting device and an address detecting device. The sample inspecting device comprises a first light source 102, a first detector 104, a first beam splitting element 106 and a first objective lens 110. The address detecting device comprises a second light source 142, a second detector 144, a second beam splitting element 146 and a second objective lens 140.

The optical equipment 1 may be used for inspecting a specimen 12 having an inspected site 12A and an address coding site 12B. In an embodiment, a sample S is placed on the inspected site 12A having several sampling points (not illustrated), and the address coding site 12B has several address codes (not illustrated). A beam of the first light source 102 is focused on the sample S by the first objective lens 110, and a beam of the second light source 142 is focused on the address coding site 12B by the second objective lens 140 simultaneously. The first beam splitting element 106 is such as a dichroic mirror. As indicated in FIG. 1, the first beam splitting element 106 may be used for reflecting the beam of the first light source 102 to the first objective lens 110 and then focusing the reflected beam on the inspected site 12A, and the second beam splitting element 146 may be used for reflecting the beam of the second light source 142 to the second objective lens 140 and then focusing the reflected beam on the address coding site 12B.

In an embodiment, the first light source 102 provides a beam having a first wavelength, the second light source 142 provides a beam having a second wavelength, and the first wavelength and the second wavelength may be the same or different, but the disclosure is not limited thereto. If the first wavelength and the second wavelength are the same, the first light source 102 and the second light source 142 may be integrated as one light source to save space and cost. If the first wavelength and the second wavelength are not the same, then respective light sources with suitable wavelengths are provided according to the features of the inspected site 12A and the address coding site 12B. For example, if the sample is a biological sample with a fluorescent mark, then the first wavelength of the first light source 102 must be a specific wavelength capable of exciting the said fluorescent mark. The first wavelength of the first light source 102 may not be suitable for detecting the address coding site 12B. Therefore, the first light source 102 and the second light source 142 may be applied in a wider range of inspection and address coding by using independent light sources.

In the present embodiment, the address coding site comprises address codes having different reflective indexes or optical polarization directions. As indicated in FIG. 1, the controller 160 controls the first beam L1 of the first light source 102 to be focused on different sampling points of the sample S and then correspondingly generates several first optical signals 51, which may be transmitted to the first detector 104 through the first beam splitting element 106. Moreover, the controller 160 may control the second beam L2 of the second light source 142 to be focused on those corresponding address codes of the address coding site 12B and then correspondingly generates several second optical signal S2, which may be transmitted to the second detector 144 through the second beam splitting element 146.

In the present embodiment, the actuator 108 is disposed near the first objective lens 110 and the second objective lens 140 for receiving commands from the controller 160 to control the movements of the first objective lens 110 and the second objective lens 140. The relative positions between the first objective lens 110 and the second objective lens 140 are fixed, so that the first objective lens 110 and the second objective lens 140 are displaced with respect to the specimen 12, and several sample inspected information and its corresponding address information can thus be obtained.

It is noted that there is a fixed relative position between each sampling point on which the first beam L1 is focused and the address code on which its corresponding second beam L2 is focused. The controller 160 controls the first objective lens 110 and the second objective lens 140 to move their focusing positions simultaneously, and the fixed relative position still does not change. The processing module 180 may obtain the registered image or signal information of the specimen according to the first optical signals S1 and the second optical signals S2.

As indicated in FIG. 1, the processing module 180 may comprise a processing unit 182, a calculator 184 and a storage unit 186. The processing unit 182, coupled to the first detector 104 and the second detector 144, is realized by such as a microprocessor or a processor. The calculator 184 is realized by such as a computer or a central processing unit (CPU). The storage unit 186 is realized by such as a memory, a magnetic tape, a magnetic disc or an optical disc. The storage unit 186 is selectively disposed on and coupled to the calculator 184.

In the present embodiment, the calculator 184 commands the controller 160 to adjust the focusing positions of the first objective lens 110 and the second objective lens 140. Furthermore, the controller 160 controls the scan path of the first beam L1 of the first light source 102 to pass through the sampling points, so that the first beam L1 focusing on the sampling points is reflected as the first optical signals S1. Meanwhile, the controller 160 controls the scan path of the second beam L2 of the second light source 142 to pass through the address codes, so that the second beam L2 focusing on the address codes is reflected as the second optical signals S2. After that, the processing unit 182 receives the first optical signals S1 and the second optical signals S2. Since the relative position between each sampling point and its corresponding address code is fixed, a sample inspected result may be generated according to the received first optical signals S1, and an address of the corresponding sampling point may be generated according to the received second optical signals S2. Then, the calculator obtains the registered image or signal information of the specimen according to the said inspected result and its address information. The storage unit 186 may receive and store the registered image or signal information.

Referring to FIG. 2, the optical equipment 2 comprises an optical device 20, a controller 260 and a processing module 280. The controller 260 is such as a circuit comprising the actuator 208, and the controller 260 can be integrated within the processing module 280. The optical device 20 comprises a sample inspecting device and an address detecting device. The sample inspecting device comprises a first light source 202, a first detector 204, a first beam splitting element 206 and a first objective lens 210. The address detecting device comprises a second light source 242, a second detector 244, a second beam splitting element 246 and a second objective lens 240.

The optical equipment 2 may be used for inspecting a specimen 22 having an inspected site 22A and an address coding site 22B. The processing module 280 may comprise a processing unit 282, a calculator 284 and a storage unit 286. The processing unit 282 is coupled to the first detector 204 and the second detector 244. The elements and method of the optical equipment 2 for inspecting the specimen 22 are similar to that of the optical equipment 1 except that the controller 260 is used for controlling the movement of the entire optical device 20, so that the optical device 20 is displaced with respect to the specimen 22 and several sample inspected results and their addresses can thus be obtained. The controller 260 controls the actuator 208 to move the entire optical device 20, such that the entire optical device 20 can be moved along a direction perpendicular to the optical axis of the first beam L1 of the first light source 202 and along a direction parallel to the optical axis of the first beam L1 of the first light source 202, for scanning the specimen 22. Then, the processing module 280 obtains the sample inspected results and their corresponding address information of the specimen 22 according to the first optical signals S1 and the second optical signals S2.

Referring to FIG. 3, the optical equipment 3 comprises an optical device 20, a controller 260 and a processing module 280. The optical equipment 3 is similar to the optical equipment 2. The same elements between the optical equipment 2 and the optical equipment 3 are represented by same reference numbers, and the similarity are not repeated here. A difference between the optical equipment 3 in FIG. 3 and the optical equipment 2 in FIG. 2 is that the actuator 308 is used for controlling the specimen 22 so that the specimen 22 can be moved along a direction perpendicular to the optical axis of the first beam L1 of the first light source 202 and along a direction parallel to the optical axis of the first beam L1 of the first light source 202.

Figure 4:
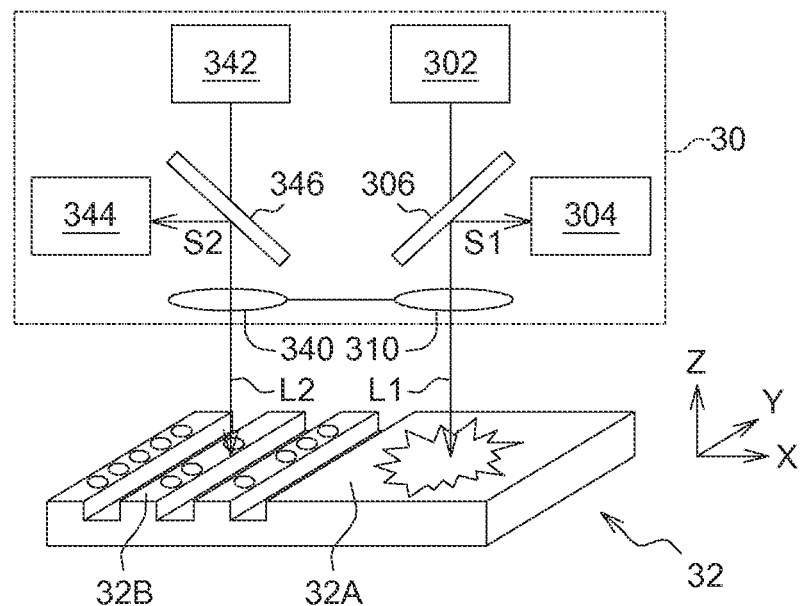
FIGS. 4~9 show schematic diagrams of an optical device and an inspected specimen according to different embodiments of the disclosure.

FIG. 4~9 respectively show a schematic diagram of an optical device and an inspected specimen according to different embodiments of the disclosure. Referring to FIG. 4. The optical device 30 comprises a sample inspecting device and an address detecting device. The sample inspecting device comprises a first light source 302, a first detector 304, a first beam splitting element 306 and a first objective lens 310. The address detecting device comprises a second light source 342, a second detector 344, a second beam splitting element 346 and a second objective lens 340. The optical device 30 may replace the optical device 10 or the optical device 20 in the optical equipment 1~3.

The optical equipment of the optical device 30 may be used for inspecting a specimen 32 having an inspected site 32A and an address coding site 32B. The elements and method of the optical device 30 for inspecting the specimen 32 are similar to that of the optical devices 10 and 20 except that in the optical device 30, the position of the first light source 302 swaps with that of the first detector 304 and the position of the second light source 342 swaps with that of the second detector 344. Therefore, the transmission paths of the first optical signals S1 and the second optical signals S2 are different from that of the optical device 10 of FIG. 1 and the optical device 20 of FIG. 2~3.

Figure 5:
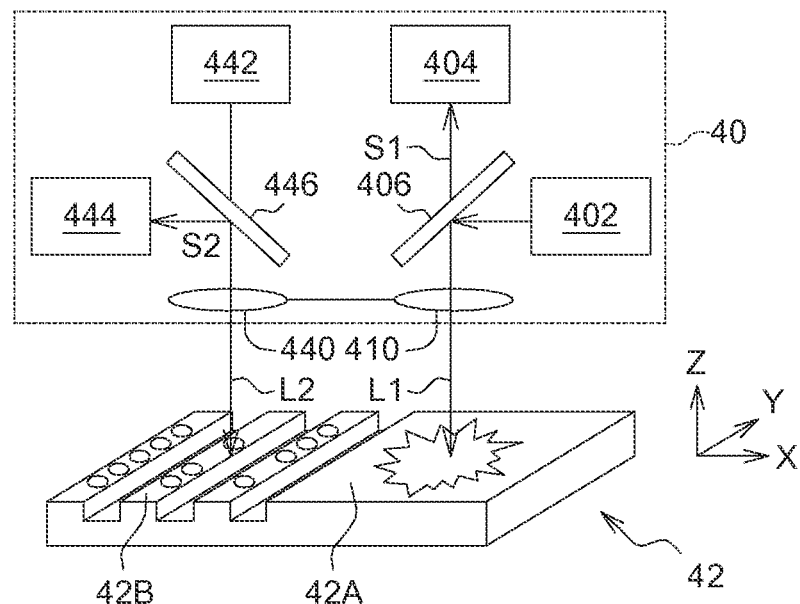

Referring to FIG. 5. The optical device 40 comprises a sample inspecting device and an address detecting device. The sample inspecting device comprises a first light source 402, a first detector 404, a first beam splitting element 406 and a first objective lens 410. The address detecting device comprises a second light source 442, a second detector 444, a second beam splitting element 446 and a second objective lens 440. The optical device 40 may replace the optical device 10 or the optical device 20 in the optical equipment 1~3.

The optical equipment of the optical device 40 may be used for inspecting a specimen 42 having an inspected site 42A and an address coding site 42B. The elements and method of the optical device 40 for inspecting the specimen 42 are similar to that of the optical device 30 except that in the optical device 40, the position of the first light source 402 swaps with that of the first detector 404. Therefore, the transmission path of the first optical signals S1 is different from that of the optical device 30 of FIG. 4.

Figure 6:
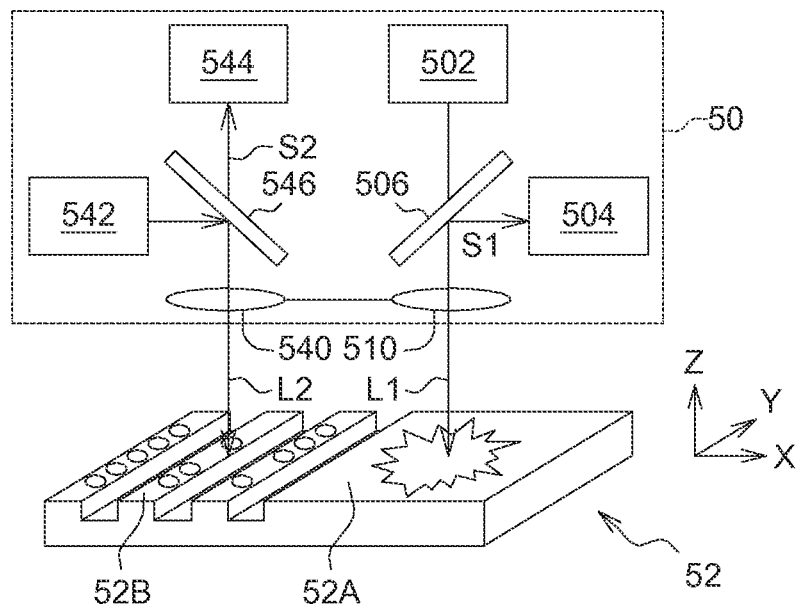

Referring to FIG. 6. The optical device 50 comprises a sample inspecting device and an address detecting device. The sample inspecting device comprises a first light source 502, a first detector 504, a first beam splitting element 506 and a first objective lens 510. The address detecting device comprises a second light source 542, a second detector 544, a second beam splitting element 546 and a second objective lens 540. The optical device 50 may replace the optical device 10 or the optical device 20 in the optical equipment 1~3.

The optical equipment of the optical device 50 may be used for inspecting a specimen 52 having an inspected site 52A and an address coding site 52B. The elements and method of the optical device 50 for inspecting the specimen 52 are similar to that of the optical device 30 except that in the optical device 50, the position of the second light source 542 swaps with that of the second detector 544. Therefore, the transmission path of the second optical signals S2 is different from that of the optical device 30 of FIG. 4.

Figure 7:
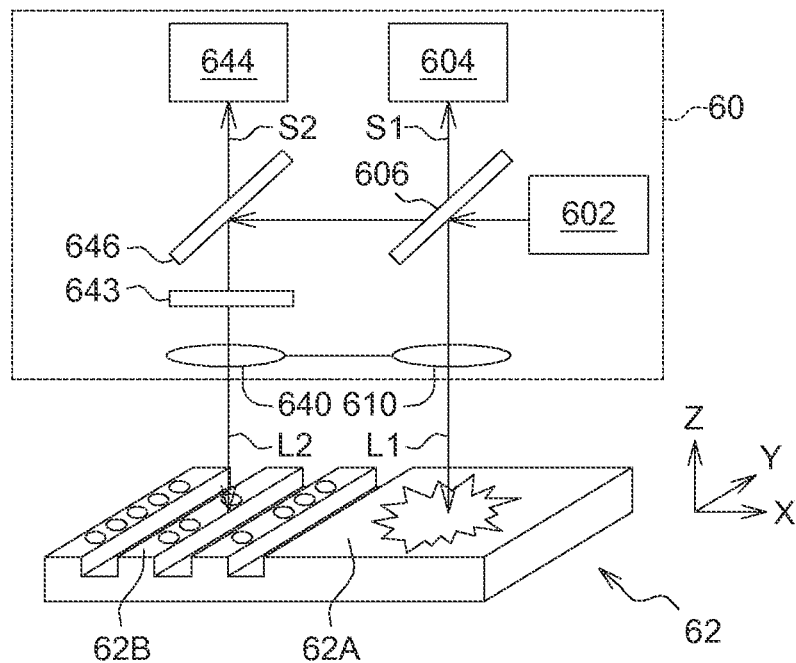

Referring to FIG. 7, the optical device 60 comprises a sample inspecting device and an address detecting device. The sample inspecting device comprises a first light source 602, a first detector 604, a first beam splitting element 606 and a first objective lens 610. The address detecting device comprises a second detector 644, a second beam splitting element 646 and a second objective lens 640. The optical device 60 may replace the optical device 10 or the optical device 20 in the optical equipment 1~3.

The optical equipment of the optical device 60 may be used for inspecting a specimen 62 having an inspected site 62A and an address coding site 62B. The elements and method of the optical device 60 for inspecting the specimen 62 are similar to that of the optical devices 10 and 20 except that the optical device 60 only has a first light source 602 and the second light source is omitted. That is, the first light sources 102 and 202 and the second light sources 142 and 242 of the optical device 10~20 of FIGS. 1~3 are integrated as one single first light source 602 for saving both space and costs. In the present embodiment, the second beam splitting element 646 is realized by such as a polarization beam splitter (PBS), and a one-quarter wavelength plate 643 is disposed between the second beam splitting element 646 and the second objective lens 640 for increasing the energy efficiency in transmitting the second optical signal S2 to the second detector 644.

Figure 8:
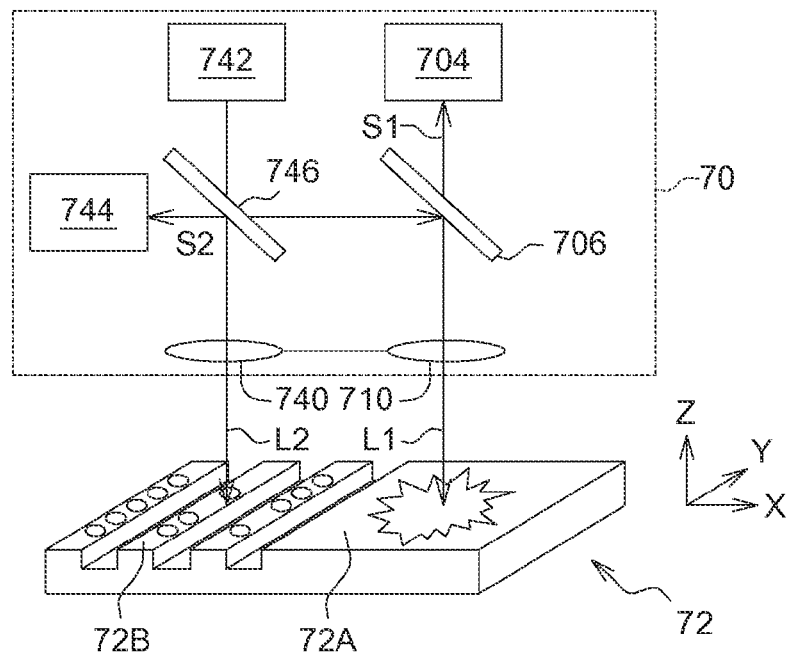

Referring to FIG. 8. The optical device 70 comprises a sample inspecting device and an address detecting device, and the sample inspecting device comprises a first detector 704, a first beam splitting element 706 and a first objective lens 710. The address detecting device comprises a second light source 742, a second detector 744, a second beam splitting element 746 and a second objective lens 740. The optical device 70 may replace the optical device 10 or the optical device 20 in the optical equipment 1~3.

The optical equipment of the optical device 70 may be used for inspecting a specimen 72 having an inspected site 72A and an address coding site 72B. The elements and method of the optical device 70 for inspecting the specimen 72 are similar to that of the optical devices 10 and 20 except that the optical device 70 only has a second light source 742 and the first light source is omitted. That is, the first light sources 102 and 202 and the second light sources 142 and 242 of the optical device 10~20 of FIGS. 1~3 are integrated as one single second light source 742 for saving both space and costs.

Figure 9:
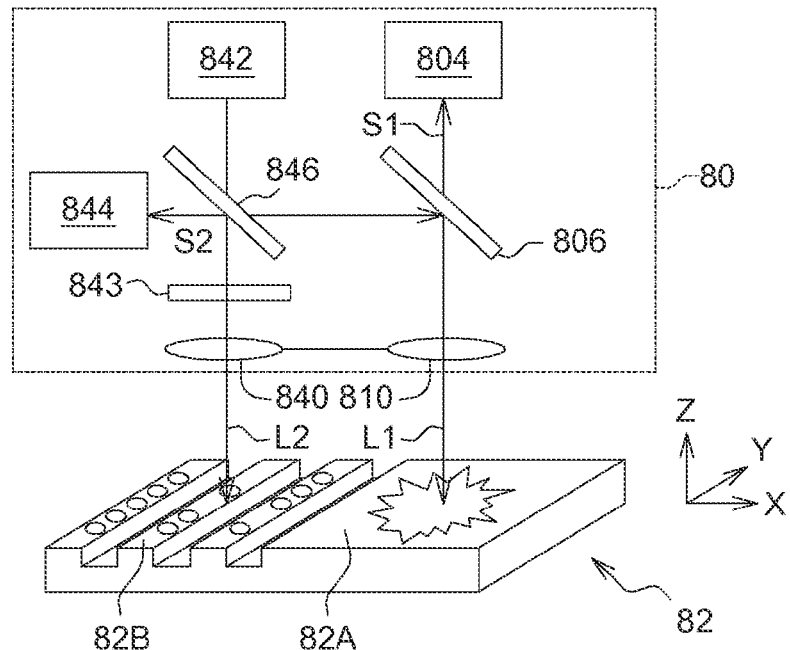

Referring to FIG. 9, the optical device 80 comprises a sample inspecting device and an address detecting device.

The sample inspecting device comprises a first detector 804, a first beam splitting element 806 and a first objective lens 810. The address detecting device comprises a second light source 842, a one-quarter wavelength plate 843, a second detector 844, a second beam splitting element 846 and a second objective lens 840. The optical device 80 may replace the optical device 10 or the optical device 20 in the optical equipment 1~3.

The optical equipment of the optical device 80 may be used for inspecting a specimen 82 having an inspected site 82A and an address coding site 82B. The elements and method of the optical device 80 for inspecting the specimen 82 are similar to that of the optical devices 10 and 20 except that the optical device 80 only has a second light source 842 and the first light source is omitted for saving both space and costs. In the present embodiment, the second beam splitting element 846 is realized by such as a polarization beam splitter (PBS), and the one-quarter wavelength plate 843 is disposed between the second beam splitting element 846 and the second objective lens 840 for increasing the energy efficiency in transmitting the second optical signal S2 to the second detector 844.

Figure 10A:
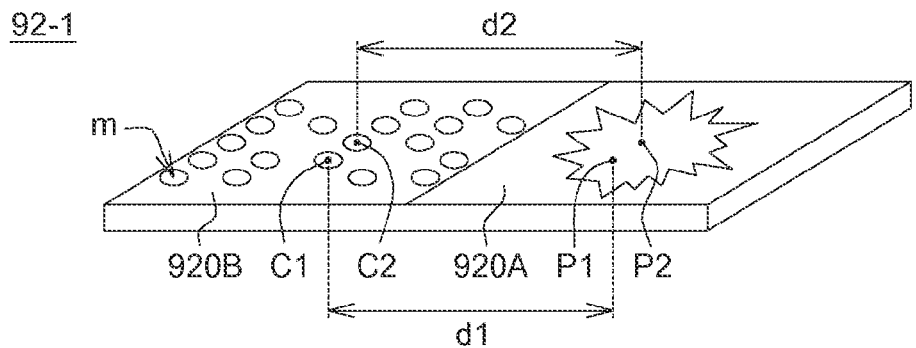
FIGS. 10A~10D show schematic diagrams of an inspected specimen according to different embodiments of the disclosure.

FIG. 10A~10D show schematic diagrams of a specimen according to different embodiments of the disclosure. The specimens 92-1~92-4 each having inspected sites 920A~926A and address coding sites 920B~926B may be used in the optical devices 10~80 of any embodiments of the disclosure. Referring to FIG. 10A, several address codes C1~C2 of the address coding site 920B of the specimen 92-1 respectively correspond to several micro-structures m, and may be realized by such as several pits arranged according to an arrangement associated with address encoding. Furthermore, when the focusing point of the first light source is moved to the sampling point P2 from the sampling point P1, the focusing point of the second light source is correspondingly moved to the address code C2 from the address code C1, and the distance dl between the sampling point P1 and the address code C1 is equal to the distance d2 between the sampling point P2 and the address code C2.

Figure 10B:
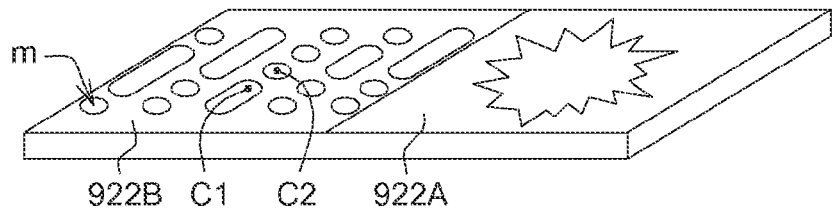
Figure 10C:
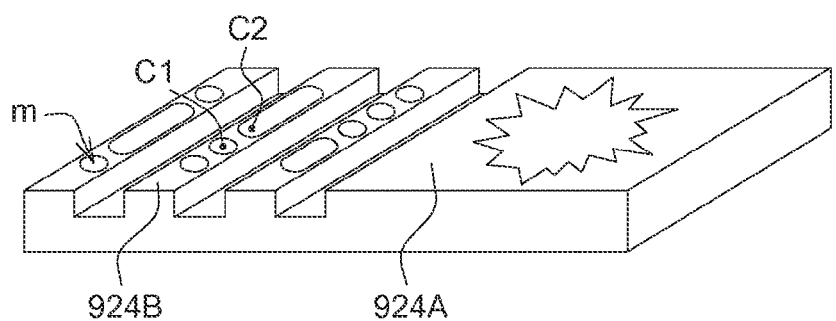
Figure 10D:
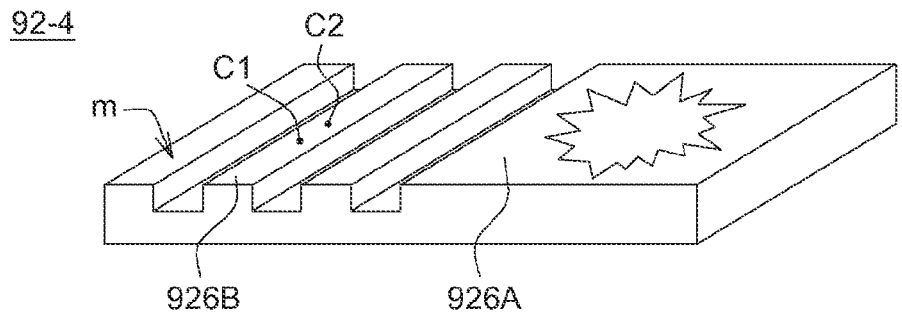

Referring to FIG. 10B. The specimen 92-2 is similar to the specimen 92-1 except that the micro-structures m corresponding to the address codes C1~C2 are realized by pits and long pits arranged in a specific manner. The micro-structures m may also be realized by holes of any shapes (not illustrated), and the disclosure is not limited thereto. Referring to FIG. 10C. The micro-structures m corresponding to the address codes C1~C2 may also be mixed with several tracks and pits (including pits or long pits) or holes of any shapes (not illustrated). Referring to FIG. 10D. The micro-structures m corresponding to the address codes C1~C2 may also be realized by several tracks each having several coding structures or address coding information.

In another embodiment, the address codes C1~C2 may also correspond to several address coding features having different reflective indexes or optical polarization directions. In other words, the address codes C1~C2 do not have to correspond to the micro-structures of FIG. 10A~10D as long as the beam may radiate the address codes C1~C2 to generate signals having different light intensities. In other words, any arrangement of the address codes allowing the beam focused on different address codes to be reflected as several optical signals whose energy levels are different would do.

Figure 11:
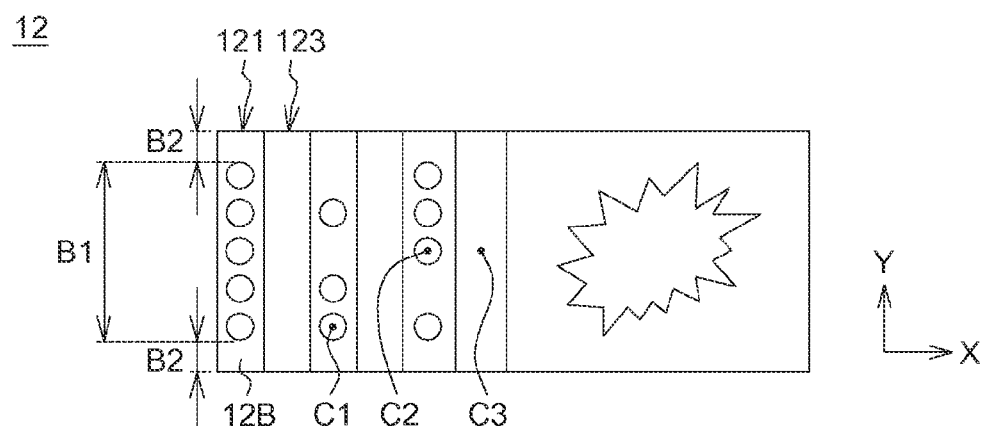
FIG. 11 shows a top view of an inspected specimen according to an embodiment of the disclosure.

FIG. 11 shows a top view of a specimen according to an embodiment of the disclosure. The method for inspecting the addressing specimen 12 by the optical equipment 1 is elaborated below with the exemplification of the optical equipment 1 of FIG. 1. Referring to both FIG. 1 and FIG. 11. The specimen 12 (such as a test slide) has an address coding site 12B having several address codes C1~C3 and corresponds to the grooves 123 and the lands 121 having several micro-structures. The controller 160 controls the second beam L2 of the second light source 142 to scan the address coding structure of respective groove 123 and land 121 so as to obtain the address coding information. Moreover, the controller 160 controls the beam to cross over the grooves 123 and the lands 121 to perform scanning to obtain a track counting information.

In an embodiment, different address coding structures are disposed on respective grooves 123 and lands 121 of the address coding site 12B according to the encoding method. The address coding structures on each track are distributed in the block B1 along the Y-axis direction (that is, the track direction of the groove 123 and the land 121) of the specimen 12, wherein the block B2 on the two ends of the track do not have any coding structures disposed thereon.

Figure 12:
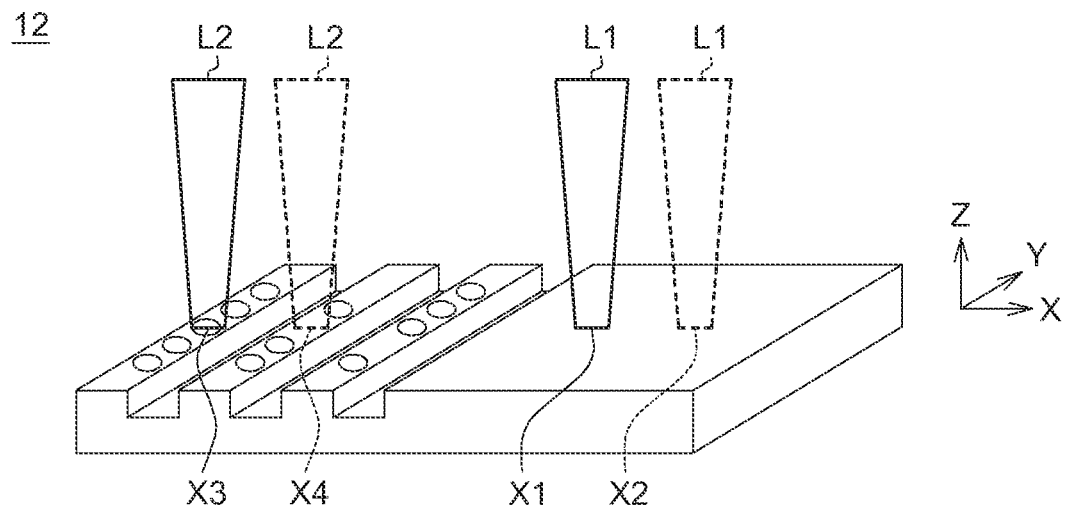
FIG. 12 shows a schematic diagram of a second beam being focused on different address codes of the address coding site of an inspected specimen according to an embodiment of the disclosure.

FIG. 12 shows a schematic diagram of a second beam being focused on different positions of a specimen 12 according to an embodiment of the disclosure. As indicated in FIG. 12, when the first beam L1 is moved to the second position X2 from the first position X1 and the second beam L2 is correspondingly moved to the fourth position X4 from the third position X3, the distance between the first position X1 and the third position X3 is equal to the distance between the second position X2 and the fourth position X4.

Figure 13:
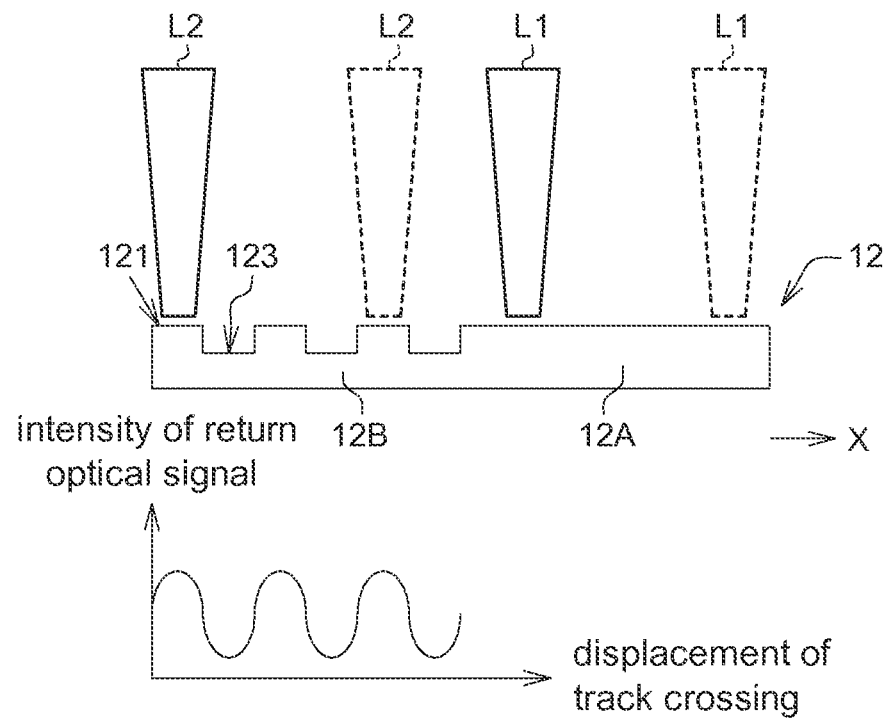
FIG. 13 shows a schematic diagram of the intensity of a second optical signal corresponding to a second beam being focused on the block B2 of FIG. 11 and crossing over different tracks.

FIG. 13 shows a schematic diagram of the intensity of a second optical signal corresponding to a second beam L2 being focused on the block B2 of FIG. 11 and crossing over different tracks along the X-axis direction of the specimen 12. Referring to FIG. 13. The second beam L2 is focused on the block B2 and crosses over different tracks along the X-axis direction of the specimen 12. When the second beam L2 is focused on the land 121, the light intensity, which denotes the track information and is detected by the second detector 144 (illustrated in FIG. 1), generates signals having strongest intensity. When the second beam L2 is focused on the groove 123 between two adjacent lands 121, the light intensity, which denotes the track information and is detected by the second detector 144, generates signals having weakest intensity. Based on the difference in the light intensity denoting the track information, the track position on which the second beam L2 is focused may be estimated. Based on the count of the wave patterns of the light intensities denoting the track crossing information, the number of tracks being crossed over can be estimated. Furthermore, during the scanning process (for example, the second beam L2 is moved along the Y-axis direction of the specimen 12), the light intensity denoting the track information may maintain at the strongest or the weakest level by method of servo control (is realized by such as push-pull method or differential phase detection method well-known in optical storage). Thus, the specific position of the groove and the land being scanned can be obtained, and accurate addressing information can be obtained through decoding by determining the address coding structure on the track.

Figure 14:
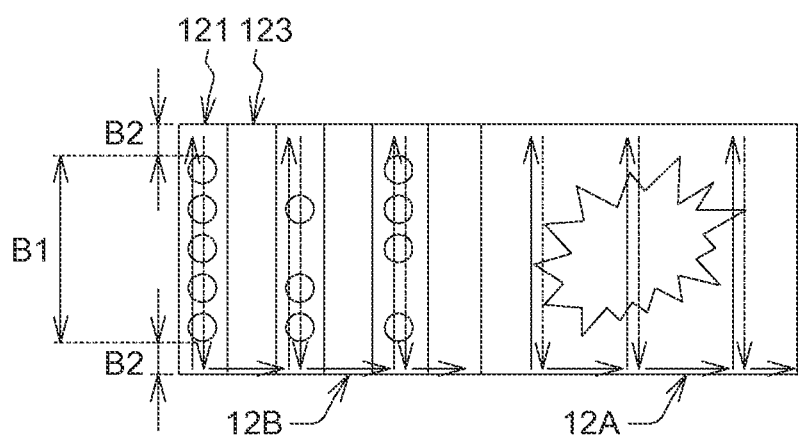
FIGS. 14~15 shows schematic diagrams of a scan path of an optical equipment according to different embodiments of the disclosure.
Figure 15:
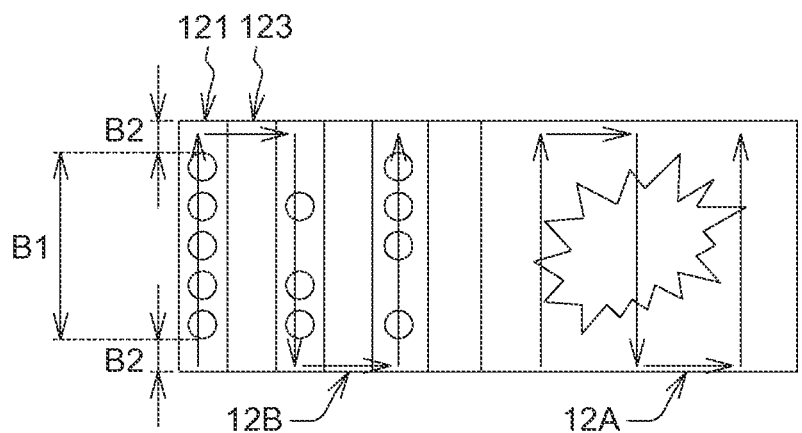

FIGS. 14~15 respectively show a schematic diagram of a scan path of an optical equipment according to different embodiments of the disclosure. Referring to FIG. 14. The second beam L2 scans from one end of the groove or land of the address coding site 12B to the other end, returns by following the original path, and crosses the track in the block B2 of the address coding site 12B. Then, the above scanning process is repeated. Referring to FIG. 15. The second beam L2 alternatively scans from one end of the groove or land of the address coding site 12B to the other end, crosses the track on the block B2 of the address coding site 12B, and scans from one end of the address encoding track to the other end in an opposite direction. Then, the above S-shaped track crossing and scanning are repeated.

In the present embodiment, the specimens 12-1 and 12-2 may be scanned according to a scan path along the land structure or the groove structure of the address coding site 12B. Also, the interval between the grooves or between the lands of the address coding site 12B may be reduced so as to increase the scan resolution (that is, the density of image or signal sampling points of the sample inspected site 12A of the specimen 12). Alternatively, the address coding structures may be distributed over both the grooves and lands of the address coding site 12B of FIGS. 14~15. Meanwhile, the scan resolution will be two times higher than that of the address coding site 12B illustrated in FIGS. 14~15.

Figure 16:
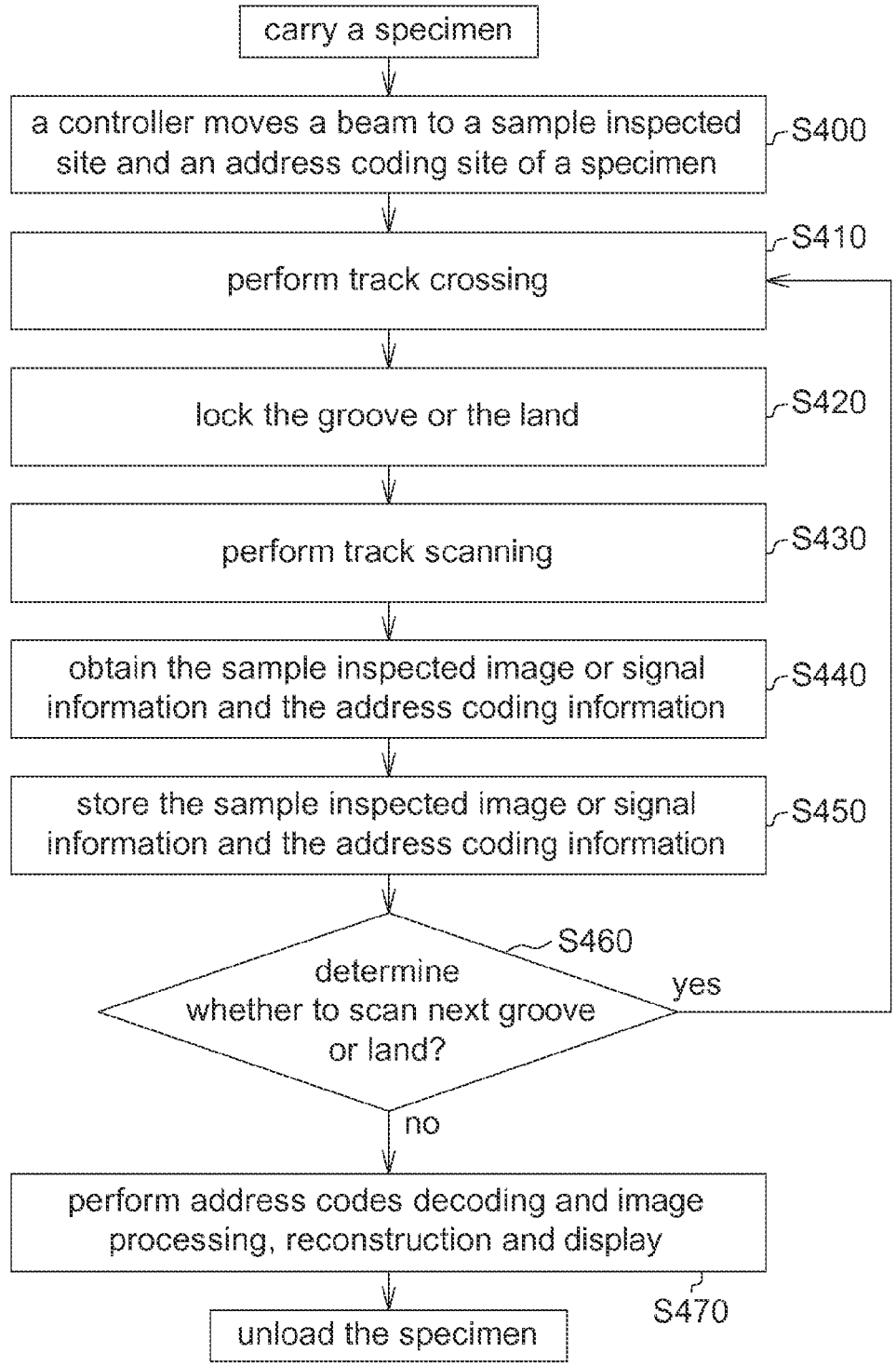
FIG. 16 shows a flowchart of an address registration method according to an embodiment of the disclosure.

FIG. 16 shows a flowchart of an address registration method according to an embodiment of the disclosure. Firstly, a specimen is carried. Next, the method proceeds to step S400, a beam is moved to a sample inspected site and an address coding site of a specimen by a controller. Then, the method proceeds to step S410, track crossing is performed. Then, the method proceeds to step S420, the groove or the land is locked. After that, the method proceeds to step S430, a track scanning process is performed. Afterwards, the method proceeds to step S440, the sample inspected image or signal information and the address coding information are obtained. Then, the method proceeds to step S450, the sample inspected image or signal information and the address coding information are stored. Then, the method proceeds to step S460, whether to scan next groove or land is determined. If so, the method returns to step S410, otherwise, the method proceeds to step S470, address codes decoding and image processing, reconstruction and display are performed. Lastly, the specimen is unloaded. FIG. 16 only shows a flowchart of an address registration method according to an embodiment of the disclosure. However, the above disclosed embodiments of the disclosure are also applicable to the address registration method, and the disclosure is not limited thereto.

An optical equipment and an address registration method are disclosed in above embodiments of the disclosure. A beam is focused on a sample placed on an inspected site of a specimen for capturing an image or detecting a signal, and another beam is focused on the address coding site adjacent to the inspected site to obtain address coding information. Since the two beams are adjacent and synchronized, the inspected image or signal of each sampling point has corresponding address code, such that the image or signal denoted by the sample inspected information has addressing features. Besides, the sampling point can be any position, and images can be captured and signals can be detected on several different sampling points. Furthermore, random noises can be eliminated by taking average on the values detected on the same position so as to produce a result with high signal noise (S/N) ratio. Or, under the circumstance that the signal is feeble, a result with sufficient intensity and free of position offset can be obtained through the integral over the time. Without reducing the resolution level, several small-area images can be stitched to form one large-area image by way of address registration.

Since the two beams focused on the inspected site and the address coding site are adjacent and synchronized, a simple and linear position relationship is formed between the position of the actual sampling point and the address obtained by detecting and decoding the optical signal reflected from the beam of the address coding site and, smaller error accumulation and higher positioning precision are thus achieved. Since the inspected site and the address coding site are on the same specimen or slide (carrying container) at the same time, the inspection is traceable, repeatable, and free of image offset despite that the specimen or slide is removed from the original inspecting equipment in the course of detection and is placed back latter. This feature is very convenient for dynamic comparison of the specimen over the time, and for image or signal processing as well. Apart from being used in optical inspection, the optical equipment of the above embodiments of the disclosure may also be used in other optical operations such as optical therapy, optical tweezers and so on for providing accurate positioning required in the operating process.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. An optical equipment used for inspecting and addressing a sample placed on an inspected site of a specimen having the inspected site and an address coding site, wherein the optical equipment comprises:
   an optical device comprising:
      a light source;
      a sample inspecting device comprising a first objective lens and a first detector, wherein a beam of the light source is focused on the sample placed on the inspected site by the first objective lens; and
      an address detecting device comprising a second objective lens and a second detector, wherein a beam of the light source is focused on the address coding site by the second objective lens; and
   a processing module used for controlling the beam of the light source to be focused on a plurality of sampling points of the inspected site to generate a plurality of first optical signals, and controlling the beam of the light source to be focused on a plurality of address codes of the address coding site to generate a plurality of second optical signals, and wherein all of relative positions between each sampling point and its corresponding address code are the same so as to calculate and register addressing image or signal information of the specimen according to the first and the second optical signals.

2. The optical equipment according to claim 1, wherein the light source comprises:
   a first light source providing a beam having a first wavelength; and
   a second light source providing a beam having a second wavelength, wherein the first optical signals are generated after the beam of the first light source is focused on the sampling points of the inspected site, and the second optical signals are generated after the beam of the second light source is focused on the address codes of the address coding site.

3. The optical equipment according to claim 1, wherein the first optical signals are generated after the beam of the light source is focused on the inspected site, the second optical signals are generated after the beam of the light source is focused on the address coding site, and the wavelength of one of the second optical signals is different from the wavelength of one of the first optical signals.

4. The optical equipment according to claim 1, wherein the processing module comprises:
   a controller for controlling the beam of the light source to be focused on the sampling points of the inspected site to generate and output the first optical signals to the first detector, and controlling the beam of the light source to be focused on the address codes of the address coding site to generate and output the second optical signals to the second detector;

a processing unit coupled to the first detector and the second detector for receiving the first and the second optical signals and accordingly obtaining sample inspected information and its corresponding address coding information;

a calculator coupled to the controller and the processing unit for commanding the controller to adjust a focusing position of the beam of the light source and decoding the address coding information to an address information; and a storage unit coupled to the calculator for storing the sample inspected information and the address information.

5. The optical equipment according to claim 4, wherein the controller comprises an actuator on which the first objective lens and the second objective lens are disposed, and the actuator further controls the first objective lens and the second objective lens to move along a direction perpendicular to an optical axis of the light source and parallel to the optical axis of the light source.

6. The optical equipment according to claim 4, wherein the controller comprises an actuator for controlling the specimen or the optical device to move along a direction perpendicular to an optical axis of the light source and parallel to the optical axis of the light source.

7. The optical equipment according to claim 1, wherein the optical device further comprises:
    a first beam splitting element for transmitting the beam of the light source to the inspected site and transmitting the first optical signals to the first detector; and
    a second beam splitting element for transmitting the beam of the light source to the address coding site and transmitting the second optical signals to the second detector.

8. The optical equipment according to claim 7, wherein the first beam splitting element is a dichroic mirror.

9. The optical equipment according to claim 7, wherein the second beam splitting element is a polarization beam splitter, and the optical equipment further comprises:
    a one-quarter wavelength plate disposed between the second beam splitting element and the second objective lens.

10. The optical equipment according to claim 1, wherein the address codes correspond to a plurality of micro-structures, and the beam of the light source, when focused on the address codes, is reflected as the second optical signals by the micro-structures.

11. The optical equipment according to claim 10, wherein the micro-structures comprise at least one of pit, long pit, hole of any shapes, groove and land.

12. The optical equipment according to claim 1, wherein the address coding site comprise the plurality of address codes having different reflective indexes or optical polarization directions.

13. The optical equipment according to claim 1, wherein the inspected site and the address coding site are adjacent to each other.

14. An address registration method comprising following steps:
    providing an optical equipment comprising an optical device and a processing module, wherein the optical device comprises a light source, a sample inspecting device and an address detecting device, the sample inspecting device comprises a first objective lens and a first detector, and the address detecting device comprises a second objective lens and a second detector;
    providing a specimen having an inspected site and an address coding site, wherein the inspected site has a plurality of sampling points and the address coding site has a plurality of the address codes, and a sample is placed on the inspected site;
    focusing a beam of the light source on the sample by the first objective lens, and simultaneously focusing a beam of the light source on the address coding site by the second objective lens;
    generating and outputting a plurality of first optical signals by the processing module after controlling the beam of the light source to be focused on the sampling points of the inspected site, and generating and outputting a plurality of second optical signals by the processing module after controlling the beam of the light source to be focused on the address codes of the address coding site, wherein all of relative positions between each sampling point and its corresponding address code are the same; and
    calculating and registering the an addressing information of the specimen by the processing module according to the first and the second optical signals.

15. The address registration method according to claim 14, wherein the light source comprises a first light source having a first wavelength beam and a second light source having a second wavelength beam, the first optical signals are generated after the first wavelength beam is focused on the sampling points of the inspected site, and the second optical signals are generated after the second wavelength beam is focused on the address codes of the address coding site.

16. The address registration method according to claim 14, wherein the processing module comprises a controller, a processing unit, a calculator and a storage unit, the processing unit is coupled to the first detector and the second detector, and the processing of the address information comprises:
    commanding the controller by the calculator to adjust a focusing position of the beam of the light source;
    controlling a scan path of the beam of the light source by the controller to pass through the sampling points, wherein the beam of the light source is reflected as the first optical signals from the sampling points to the first detector;
    controlling the scan path of the beam of the light source by the controller to simultaneously pass through the address codes having different reflective indexes or optical polarization directions, wherein the beam of the light source is reflected as the second optical signals from the address codes to the second detector;
    receiving the first and the second optical signals by the first and second detectors and the processing unit for generating a sample inspected information and its corresponding address coding information;
    decoding the address coding information to the address information by the calculator; and
    storing the sample inspected information and the address information.

17. The address registration method according to claim 16, wherein the address coding site comprises a plurality of grooves and lands, each of the grooves and lands having a plurality of address coding structures, and the step of controlling the scan path of the beam comprises:
    controlling the beam of the light source to scan across the grooves and the lands to obtain a track information; and controlling the beam of the light source to scan the address coding structures on one of the grooves or one of the lands to obtain the address coding information.

18. The address registration method according to claim 14, wherein the optical device further comprises a first beam splitting element and a second beam splitting element, and the step of focusing the beam of the light source comprises:
   using the first beam splitting element to transmit the beam of the light source to the first objective lens and then focus the beam of the light source on the inspected site; and
   using the second beam splitting element to transmit the beam of the light source to the second objective lens and then focus the beam of the light source on the address coding site.

19. The address registration method according to claim 18, wherein the first optical signals are transmitted to the first detector by the first beam splitting element, and the second optical signals are transmitted to the second detector by the second beam splitting element.

20. The address registration method according to claim 14, wherein the address codes correspond to at least one of a plurality of micro-structures and a plurality of address coding features having different reflective indexes or optical polarization directions, the beam of the light source after being focused on the address codes is reflected as the second optical signals having different energy levels.

* * * * *